(12) United States Patent
Gibson et al.

(10) Patent No.: US 6,931,401 B2
(45) Date of Patent: Aug. 16, 2005

(54) METHODS AND APPARATUS FOR HIGH-SPEED APPROXIMATE SUB-STRING SEARCHES

(75) Inventors: Michael A. Gibson, Sierra Madre, CA (US); Richard J. Messenger, Pasadena, CA (US); Marc A. Rieffel, Glendale, CA (US); Zheng Zhang, Pasadena, CA (US)

(73) Assignee: Paracel, Inc., Pasadena, CA (US)

( * ) Notice: Subject to any disclaimer, the term of this patent is extended or adjusted under 35 U.S.C. 154(b) by 309 days.

(21) Appl. No.: 10/139,905

(22) Filed: May 6, 2002

(65) Prior Publication Data

US 2003/0033279 A1 Feb. 13, 2003

Related U.S. Application Data

(60) Provisional application No. 60/288,465, filed on May 4, 2001.

(51) Int. Cl.[7] .............................................. G06F 17/30
(52) U.S. Cl. .......................................... 707/6; 707/101
(58) Field of Search ................... 707/1–10, 100–104.1, 707/200–205; 702/19–20

(56) References Cited

U.S. PATENT DOCUMENTS

| | | | |
|---|---|---|---|
| 6,112,288 A | 8/2000 | Ullner | 712/20 |
| 6,223,186 B1 * | 4/2001 | Rigault et al. | 707/104.1 |
| 6,421,613 B1 * | 7/2002 | Nadimpalli et al. | 702/20 |
| 6,470,277 B1 * | 10/2002 | Chin et al. | 702/19 |
| 6,691,109 B2 * | 2/2004 | Bjornson et al. | 707/4 |

OTHER PUBLICATIONS

Altschul et al. "Basic Local Alignment Search Tool" J. Mol. Biol. 215(3):403–410 (1990).
Altschul et al. "Gapped BLAST and PSI–BLAST: New Generation of Protein Database Search Programs" Nucleic Acids Research 25(17):389–3402 (1997).
Benson et al. "GenBank" Nucleic Acids Research 28(1):15–18 (2000).
Bentley. "Multidimensional Binary Search Trees Used for Associative Searching" Communications of the ACM 18(9):509–517 (1975).
Eddy. "Profile Hidden Markov Models" Bioinformatics 14(9):755–763 (1998).
Henikoff et al. "Amino Acid Substitution Matrices from Protein Blocks" Proc. Natl. Acad. Sci. USA 89:10915–10919 (1992).
Henikoff et al. "Performance Evaluation of Amino Acid Substitution Matrices" Proteins 17:49–61 (1993).

(Continued)

*Primary Examiner*—Mohammad Ali
(74) *Attorney, Agent, or Firm*—Morrison & Foerster LLP (57) ABSTRACT

A method and system for conducting sequence searches in a sequence database wherein in one embodiment, the method includes: combining a plurality of query sequences into a combined query sequence; determining a plurality of subdivisions of the sequence database; performing a plurality of searches, wherein each search includes a comparison of the combined query sequence against one of the plurality of subdivisions of the database to produce a plurality of word matches; extending the length of the plurality of word matches to produce a plurality of High-scoring Segment Pairs, combining the plurality of High-scoring Segment Pairs; and producing a plurality of reports, each report representing the highest scoring matches for one of the plurality of query sequences.

4 Claims, 4 Drawing Sheets

OTHER PUBLICATIONS

<http://www.ncbi.nlm,.nih.gov/Genbank/genbankstats.html> (visited Jul. 30, 2002).

Zhang et al. "Chaining Multiple–Alignment Blocks" J. of Computational Biology 1:217–226 (1994).

Zhang et al. "A Greedy Algorithm for Aligning DNA Sequences" J. of Computational Biology 7(1–2):203–214 (2000).

Altschul et al. "Basic Local Alignment Statistics" *Methods in Enzymology* 266:460–480 (1996).

* cited by examiner

METHODS AND APPARATUS FOR HIGH-SPEED APPROXIMATE SUB-STRING SEARCHES

RELATED APPLICATIONS

The present application claims the benefit of priority under 35 U.S.C. § 119(e) to U.S. Provisional Patent Application Ser. No. 60/288,465, entitled "Method and Apparatus for High-Speed Approximate Sub-String Searches," filed May 4, 2001, the entirety of which is incorporated by reference herein.

FILED OF THE INVENTION

The present invention relates to string searching, and more specifically to computer implemented string searching of databases.

BACKGROUND OF THE INVENTION

When a novel stretch of nucleic acid, e.g., DNA, or protein is first sequenced, its sequence is typically compared against a database of known DNA and protein information to provide a preliminary indication of the new DNA or protein's function. A researcher can then design experiments to assay the results of the database search.

As a result of the enormous improvement of DNA sequencing technology, the rate of growth of the DNA database has grown exponentially over the last decade from 1.5 million nucleotides per year in 1989 to over 1.6 billion nucleotides per year in 1999. Since 1999, entire genomes have been sequenced, including those of drosophila, mouse, and human. As the amount of known genetic sequence information increases exponentially, it becomes increasingly important to develop high speed methods to search the expanding sequence databases.

For example, GenBank, a public repository of genomic information, currently has nearly 16 GB of data, having grown from a mere 680 K in 1982 (Benson et al., *Nucleic Acids Research*, 28(1):15–18 (2000) (See also www.ncbi.nlm.nih.gov/Genbank/genbankstats.html.)). At that rate, the amount of data is doubling every 16.5 months. In 2001 alone, 3.5 million sequences totaling 3 GB of new sequence were entered into GenBank. Both public and private sequencing facilities consist of warehouse-sized factories generating data around the clock, limited only by the availability of reagents and the speed of the sequencing machines.

As more sequence data becomes available, one of the most basic problems is sequence alignment—how does a newly discovered nucleotide or amino acid sequence relate to previously known and studied data? Note that whenever the amount of sequence data doubles, the number of possible comparisons quadruples. Therefore, despite similarly impressive exponential doubling of computer speed on roughly the same time course, sequence comparison algorithms are falling farther and farther behind in their ability to find homologies for any significant part of the available data.

Much of the current research in homology searching focuses on algorithms that are more sensitive and selective—algorithms that use sophisticated techniques such as Hidden Markov Models to reduce the rate of false positives and false negatives, in other words to correctly identify weak homologies (e.g., genes in two very distantly related organisms), as described in, for example Eddy, "Profile Hidden Markov Models," *Bioinformatics*, 14(9): 755–763 (1998), the entirety of which is incorporated by reference herein. Such algorithms push the envelope of mining the maximum amount of information from the data available, and are of enormous research interest. This invention takes a different track. For many applications, existing algorithms are good enough. In particular, the BLAST (Basic Local Alignment Search Tool) family of algorithms, developed by NCBI is sufficiently sensitive and selective for most searches. See, for example, Altschul, et al., "Gapped BLAST and PSI-BLAST: new generation of protein database search programs," *Nucleic Acids Research*, 25(17): 389–3402 (1997), the entirety of which is incorporated by reference herein.

Basic Local Alignment Search Tool

Currently, the most common methods of high speed database are variants of the Basic Local Alignment Search Tool ("BLAST") described by Altschul, et al., *J. Mol. Biol.*, 215(3):403–10 (1990), the entirety of which is incorporated by reference herein. BLAST and its variants provide a fast, local alignment of sequences. BLAST programs have been written to compare protein or DNA queries with protein or DNA databases in any combination, with DNA sequences often undergoing conceptual translation before any comparison is performed.

BLAST is a heuristic that attempts to optimize a similarity measure. Specifically, BLAST identifies all local regions of similarity (called High-scoring Segment Pairs or "HSPs") which can statistically be distinguished from random alignments. BLAST permits a tradeoff between speed and sensitivity, with the setting of a "threshold" parameter, T. A higher value of T yields greater speed, but also an increased probability of missing weak similarities. The BLAST program requires time proportional to the product of the lengths of the query sequence and the database searched.

The central idea of the BLAST algorithm is that a statistically significant alignment is likely to contain a high-scoring pair of aligned words. BLAST first scans the database for words (e.g., 3 for proteins and 12 for DNA) that score at least T when aligned with some word within the query sequence. Any aligned word pair satisfying this condition is called a "hit." The second step of the algorithm checks whether each hit lies within an alignment with a score sufficient to be reported. This is done by extending a hit in both directions, until the running alignment's score has dropped more than X below the maximum score yet attained.

In its most fundamental implementation, the BLAST algorithm performs three steps: (1) compile a list of high scoring words of length w from the query sequence; (2) for each sequence in the database, scan for word hits—i.e. words from the query sequence matching words in the database sequence—with scores greater than a threshold T; (3) for each word hit, extend it in both directions to form a High Scoring Pair ("HSP") of score greater than or equal to S. The to following paragraphs describe these steps in greater detail.

In a typical BLAST implementation, the list of high scoring words is compiled into a lookup table with i rows and j columns, where i is the number of all possible words of length w, and j is the number of elements in the query sequence minus w. Because the value i represents every possible word of length w, each row in the lookup table corresponds to one word of length w. The row number corresponds to the lexical order of its corresponding word, and can be considered the "row number" for that word. For DNA sequences $i=4^w$; for protein sequences, $i=20^w$. The value j represents the number of starting positions of words of length w in the query sequence. The lookup table is initialized with all zeroes, and then populated as follows: For every word of length w in the query, look up its corresponding row. Call this row x. Call the position of the word in the query sequence y. Set the (x,y) element of the lookup table to y. Once the lookup table is populated, it is then trimmed. Rows with all zeroes, representing words not present in the query, are removed. The remaining words are then screened for significance by examining them to see if their self-similarity score meets a minimum threshold T. Similarity scores are typically calculated using a substitution matrix such as PAM120 and BLOSUM62, as described in Dayhoff et al., Atlas of Protein Sequence and Structure, Vol. 5, Suppl. 3, Ed. M. O. Dayhoff (1978); Henikoff and Henikoff, *Proc. Natl. Acad. Sci. USA,* 89: 10915–10519 (1992); and Henikoff and Henikoff, *Proteins,* 17: 49–61 (1993). These publications are incorporated by reference herein in their entireties. Rows representing words with self-scores less than T are eliminated. Finally, all columns with zeroes are eliminated. The resulting lookup table is indexed by the lexical word number of significant words, and returns the position of significant words in the query sequence.

BLAST is a heuristic algorithm, and values of w and T are chosen for an optimal mix of sensitivity, specificity, and speed. As w increases for a given value of T, specificity is increased but sensitivity is decreased. Similarly, as T decreases for a given value of w, sensitivity is increased, but specificity is decreased and run time is increased. Exemplary settings of w and T are w=4, T=17 for proteins and w=12, T=60 for DNA.

Once the lookup table is constructed, it is used for comparing the query sequence against the database. Specifically, the database is searched for all words of length w that are present in the query sequence whose self-scores are higher than the threshold T. Every word thus found is called a "hit." The output of the database search comprises a list of hits. Because the database is searched repeatedly, it is first preprocessed into a lookup table similar to that generated for the query sequence. Thus, the search process can be performed quickly by comparing the two lookup tables.

The final step is to extend each hit to form a High-scoring Segment Pair ("HSP"). Typically, the hit is extended in both directions until the similarity score between the corresponding stretches of query sequence and database sequence fall below a predetermined threshold S.

The output of a typical BLAST implementation includes descriptions of hits found in the database. For each hit, the output includes information about the sequence from which the hit came, the hit's score in bits, the probability that a given HSP or HSPs would have been found by chance, and the E-value, which is a measure of the number of matches expected to have been found by chance in a database of this size for the given score.

Previous Improvements to BLAST

Implementations of the BLAST algorithm have undergone improvements since the algorithm was first introduced. Three major improvements include the "two-hit" method for hit extension, the ability to generate gapped alignments, and a position-specific, iterated BLAST ("PSI-BLAST") that in many cases is more sensitive to weak but biologically relevant sequence similarities. These improvements are described in detail, for example, in Altschul, "Gapped BLAST and PSI-BLAST: a new generation of protein database search programs," *Nucleic Acids Research,* 25(17): 3389–3402 (1997).

Performance data of the original BLAST implementation indicate that the extension step, where hits are extended to form HSPs, consumed the greatest amount of processing time. The "two-hit" method for hit extension is a refinement on this step, which results in the generation of fewer time-consuming extension steps. Experimental evidence indicates that a typical HSP of interest is much longer than a single word pair, and may therefore comprise multiple hits on the same diagonal and within a relatively short distance of one another. The two-hit method exploits this observation by requiring the existence of two non-overlapping word pairs on the same diagonal, and within a distance A of one another, before an extension is invoked. Any hit that overlaps the most recent one is ignored. Because this method requires two hits rather than one to invoke an extension, the threshold parameter T must be lowered to retain comparable sensitivity. The effect is that many more single hits are found, but only a small fraction have an associated second hit on the same diagonal that triggers an extension. Thus, the great majority of hits may be dismissed after the minor calculation of looking up, for the appropriate diagonal, the coordinate of the most recent hit, checking whether it is within distance A of the current hit's coordinate, and finally replacing the old with the new coordinate. Empirically, the computation saved by requiring fewer extensions more than offsets the extra computation required to process the larger number of hits.

Another method of performing the extension step has been described, for example, in "Multiple sequence alignment using block chaining," Zheng Zhang, PhD dissertation, The Pennsylvania State University, UMI Dissertation Services, Ann Arbor (1996); and Zhang et al., "Chaining multiple-alignment blocks," *J. of Computational Biology,* 1:217–226 (1994). This method is based on the extension step's similarity to a known class of problems in computer science known as "block chaining," a special case of the classic optimal-path algorithm for directed, acyclic graphs. The method described above adopts a well-known technique of higher-dimensional computational geometry called K-D trees. Generally, K-D trees are used to decompose multidimensional space hierarchically into a relatively small number of cells such that no cell contains too many input objects (see Bentley, *Communications of the ACM,* 18:509–517, (1975), the entirety of which is incorporated by reference herein). In Zhang, K-D trees are used to decompose the space of possible block chains into regions, thus reducing the block chaining problem to the less computationally intensive problem of chaining regions. The use of K-D trees provides significant computational gains for multiple sequence comparison, i.e., more than two sequences are being compared to each other.

The ability to generate gapped alignments allows for significant improvements in BLAST's performance. The original BLAST program often finds several alignments involving a single database sequence which are statistically significant only when considered together. Overlooking any one of these alignments would compromise the combined result. By introducing an algorithm for generating gapped alignments, it becomes necessary to find only one rather than all the ungapped alignments subsumed in a significant, combined result. This allows the T parameter to be raised, increasing the speed of the initial database scan. One method of generating a gapped alignment employs a heuristic approach which is a simple generalization of BLAST's method for constructing HSPs. The central idea of this approach is to trigger a gapped extension for any HSP that exceeds a moderate score $S_g$, chosen so that no more than about one extension is invoked per 50 database sequences. Statistical analysis indicates that $S_g$ should be set at approximately 22 bits for a typical-length protein query. A gapped extension takes much longer to execute than an ungapped extension, but by performing very few of them the fraction of the total running time they consume can be kept relatively low. Furthermore, by seeking a single gapped alignment, rather than a collection of ungapped ones, only one of the constituent HSPs need be located for the combined result to be generated successfully. This means that a much higher chance of missing any single moderately scoring HSP can be tolerated. This permits the T parameter for the hit-stage of the algorithm to be raised substantially while retaining comparable sensitivity. For example, T can be raised from 11 to 13 for the one-hit heuristic of the original BLAST implementation.

The iterated application of BLAST to position-specific score matrices, also known as profiles or motifs, allows for database searches that are often much better able to detect weak but biologically significant relationships. One implementation of position-specific, iterated BLAST called PSI-BLAST constructs a position-specific score matrix from the output of a primary BLAST run and uses this matrix as a query for a subsequent BLAST run.

Although several refinements have increased the speed, sensitivity, and specificity of current implementations of BLAST more than three-fold when compared to the original, the exponential rate of sequence database expansion mandates continuous improvement to implementations of the algorithm.

Parallel Processing

One approach for speeding up large database searches is to use parallel processing. High performance parallel computing is accomplished by splitting up large and complex tasks across multiple processors. In a simple example, a sequence database can be subdivided into several parts, with each part assigned to a specific processing unit. The same query can then be run on all processing units simultaneously, with each processing unit having to search only a fraction of the database. In a more complex example, a task is divided into subtasks. For instance, the extension step in BLAST requires an exhaustive examination of alternative chains of HSPs. In this example, the space of possible chains is subdivided into a plurality of subspaces and each subspace is allocated to a separate processor.

While a variety of methods can be used to achieve improved performance on multiple computers, the most common way to organize and orchestrate parallel processing is to write code which automatically decomposes the problem at hand and allows the processors to communicate with each other when necessary while performing their work. In the first example above, if a processor finds a match to the query in its part of the database, it can signal that event to the other processors performing their searches. In the second example above, if a processor finds a new maximum score, it can signal that event so that other processors raise their thresholds.

Most applications of parallel processing usually require some amount of interaction between processors, so they must be able to communicate with each other to exchange information. For example, values for cells on a map may depend on the values of their nearest neighboring cells. If the map is decomposed into two pieces, each being processed on a separate CPU, the processors must exchange cell values on adjacent edges of the map. Similarly, if a sequence alignment is decomposed into several smaller local alignments, each processor handling each local alignment must be able to communicate with processors handling adjacent alignments in order to extend an alignment past its original bounds.

Several contrasting approaches to parallel processing exist. For example, parallel processing can be performed on highly specialized hardware or on commercial off-the-shelf ("COTS") hardware. BLAST and other sequence comparison and database searching algorithms have been implemented in highly-specialized, parallel processing hardware, such as PARACEL'S GENE MATCHER machine. As described in Ullner, U.S. Pat. No. 6,112,288, the entirety of which is incorporated by reference herein, PARACEL'S GENE MATCHER employs a programmable, special-purpose pipeline processing system, which includes a plurality of accelerator chips coupled in series. Each of the accelerator chips includes an instruction processor. Each of the pipeline processor segments includes a plurality of pipeline processors coupled in series. Such specialized hardware can provide significant speedups, especially for dynamic programming algorithms.

In contrast to the specialized hardware approach is the commodity parallel processing approach, which uses inexpensive, commercial off-the-shelf ("COTS") hardware. One popular approach to commodity parallel processing is the Beowulf cluster, described in Becker, et al., *Beowulf: A Parallel Workstation for Scientific Computation. Proceedings, International Conference on Parallel Processing* (1995); and M. S. Warren, et al., *Parallel supercomputing with commodity components*; H. R. Arabnia, editor, Proceedings of the International Conference on Parallel and Distributed Processing Techniques and Applications (PDPTA '97), pages 1372–1381, 1997. These publications are incorporated by reference herein in their entireties. A Beowulf-class cluster is a high-performance, massively parallel computer built primarily out of commodity hardware components, running a free-software operating system like Linux or FreeBSD, interconnected by a private, high-speed network. A typical Beowulf-class cluster comprises a plurality of interconnected PCs or workstations dedicated to running high-performance computing tasks. It is usually connected to the outside world through only a single node. A typical Beowulf-class cluster employs a popular method of inter-processor communication called message passing. Popular implementations of message passing include the Parallel Virtual Machine ("PVM") and the Message Passing Interface ("MPI").

Because commodity parallel processing hardware provides substantial performance at reasonable cost, and because exponential database growth requires substantial improvements in database searching techniques, there exists a need to improve the BLAST algorithm to increase its performance on commodity parallel processing hardware.

SUMMARY OF THE INVENTION

The invention addresses the above needs and other needs by providing a method and system that utilizes a combined hardware-software system to implement an improved BLAST algorithm that is two to three orders of magnitude faster than previous Blast algorithms executed by single desktop processors. The software component of this system is referred to herein as Paracel BLAST, and the hardware component is referred to herein as the Paracel BlastMachine. In accordance with the techniques taught herein, Paracel BLAST on the BlastMachine can handle genome-scale data sets. Algorithmic improvements and a parallel hardware architecture allow the BlastMachine to solve significantly larger problems than is possible with other techniques. In one embodiment, this system is well-suited for a first pass analysis of a genome, allowing more sophisticated, slower algorithms and also human intervention, at later stages, to fill in gaps that this first pass leaves.

In one aspect, the invention provides structures and methods for performing dynamic database splitting for parallelizing database searching.

In another aspect, the invention provides structures and methods for combining a plurality of queries into a single database search.

In another aspect, the invention provides structures and methods for efficient linking and extending High-scoring Segment Pairs to yield longer matches between a query sequence and a database sequence.

In one specific embodiment, the present invention is directed to a method for comparing a plurality of query sequences against a sequence database comprising the steps of: (a) combining said plurality of query sequences into a combined query sequence; (b) determining a plurality of subdivisions of said database; (c) performing a plurality of searches, wherein each search comprises a comparison of said combined query sequence against one of said plurality of subdivisions of said database, producing a plurality of word matches; (d) extending the length of plurality of word matches produced in step (c), producing a plurality of High-scoring Segment Pairs; (e) combining said plurality of High-scoring Segment Pairs; and (f) producing a plurality of reports, each report representing the highest scoring matches for one of said plurality of query sequences.

The plurality of sequences can be combined into a combined query sequence by any suitable method. For example, in step (a) of the present method, a plurality of sequences are combined into a combined query sequence by storing said plurality of sequences in a query lookup table and indexing each of said sequences with a query number to link each said sequence to a respective query number. The combining process can be controlled or monitored using any suitable parameters, e.g., a length parameter. More specifically, a plurality of sequences can be stored in a query lookup table until the amount of data stored in said table reaches a predetermined limit. In another example, in step (a) of the present method, a plurality of sequences can be combined by constructing a hash of multiple queries at the same time.

The database can be divided into a plurality of subdivisions by any suitable method. For example, the step of determining a plurality of subdivisions of the database can comprise specifying the size of said database in number of bases and the number of sequences in said database to calculate a statistically significant value for results produced by searching said databases. In other examples, the database can be divided into a plurality of subdivisions by making one or more of the following modifications to the basic BLAST algorithm: (i) at least one of the statistical parameters of the basic BLAST algorithm is adjusted to generate correct partial results; (ii) at least one of the input/output routines used in the basic BLAST algorithm to access the database is modified to support accessing a subset of the database; (iii) a plurality of memory images of intermediate results is produced; and/or (iv) the memory images are recombined to produce a single merged BLAST report. In a specific example, the basic BLAST algorithm is adjusted to specify both the size of the database and the number of sequences in the database to calculate the statistical significance of the results produced by searching the database. In another specific example, a command-line argument (−z) is used to specify the size in bases of the overall database and a command-line option (−s) is used to specify the number of overall sequences in the database. The values for the −z and −s parameters can be automatically calculated, if they are not otherwise provided, based on the overall size of the subsetted database. The database can also be divided into a plurality of subdivisions by specifying a first ordinal ID (x) to indicate a start of a subject of said database, and specifying a second ordinal ID (y) to indicate an end of said subset of said database, wherein said first ordinal ID ranges from 0 to N−1, wherein N is the number of sequences in the database. The database can be subdivided into pieces of any suitable sizes. For example, the database can be subdivided into pieces that are small enough to fit into RAM on the nodes.

The length of plurality of word matches can be extended in step (d) of the present method using any suitable method. For example, the extending step can comprise the steps of: (i) evaluating a set of the High-scoring Segment Pairs to determine the highest-scoring chain in said set according to a first criterion, wherein said chain comprises a subset of said set of High-scoring Segment Pairs; (ii) removing said chain from said set of High-scoring Segment Pairs; and (iii) repeating said steps (i) and (ii) until said set of High-scoring Segment Pairs is empty. Preferably, the evaluating step (i) can comprise the step of determining a subset of said set of High-scoring Segment Pairs which does not require recalculation according to a second criterion. In another example, the length of the plurality of word matches is extended using link_hsps( ). The length of the plurality of word matches can be extended on separate processors. Alternatively, the length of plurality of word matches can be extended on the same processor used to perform the database search.

The plurality of High-scoring Segment Pairs can be combined in step (d) of the present method using any suitable method. For example, the plurality of High-scoring Segment Pairs can be combined using a "pbmerge" program.

The present method can be conducted on any suitable hardware. For example, the present method can be conducted on commercial off-the-shelf ("COTS") hardware. Preferably, the present method can be conducted on a Beowulf-class parallel processing architecture.

The present method can be used to conduct searches for any query sequence in any suitable sequence database provided that the query sequence is compatible with at least some sequences contained in the database. However, although preferably in some circumstances, it is not necessary that the query sequence is compatible with all sequences contained in the database. For example, a protein sequence can be used as a query sequence to conduct a search in a database that contains protein sequences as well as nucleic acid sequences. Similarly, nucleic acid sequence, such as a DNA or an RNA sequence, can be used as a query sequence to conduct a search in a database that contains nucleic acid sequences as well as protein sequences.

The present method can be used to conduct searches in any suitable sequence databases such as databases comprising genomic, cDNA, EST sequences or a combination thereof. The present method can be used to conduct searches in a public database, e.g. GenBank, or a subscriber-only database.

In another specific embodiment, the present invention is directed to a method for conducting sequence searches in a database with a BLAST algorithm using the following steps: (a) compile a list of high scoring words of length w from a query sequence; (b) for each sequence in the database, scan for word hits with scores greater than a threshold T; and (c) for each word hit, extend it in both directions to form a High Scoring Pair ("HSP") of score greater than or equal to S, wherein the improvement comprises one or more of the followings: (i) combining a plurality of query sequences into a combined query sequence before conducting said search; (ii) determining a plurality of subdivisions of a database before conducting said search; (iii) restructuring coding so that whenever possible, a hash table stays in the processor's cache, rather than bouncing back and forth between processor and memory; and/or (iv) dividing query sequence that equals to or is longer than a megabase (one million bases or base pairs) into smaller pieces before conducting said search, e.g., by dividing said query sequence into overlapping pieces and running each piece separately in the search. Preferably, the query sequence is divided into smaller pieces by the following steps: a) dividing said query sequence into a plurality of overlapping sequences; b) removing overlapping portion from said overlapping sequences so that each overlapping portion is contained in only one overlapping sequence; and c) detecting whether the removed portions contain any HSPs that span said entire overlapping portion and if such HSPs are detected, finding the original hit that led to said HSP and extending said HSP in the context of the undivided query sequence. The query sequence can be divided into smaller pieces of any suitable sizes, e.g., about 10 kilobases (thousand bases or base pairs).

In still another specific embodiment, the present invention is directed to a system for conducting sequence searches in a database, which system comprises a manager node and a plurality of worker nodes, wherein said manager node is operatively linked to a client station and each of said worker nodes, and said system is capable of conducting sequence searches in a database according any of the above-described methods. In one example, at a hardware level, the manager module includes a manager node having a dual-cpu motherboard, RAM, disk, and network cards. Other nodes, e.g., worker nodes, include similar hardware, usually minus the disk. In one preferred example, the manager node executes a manager "daemon" (persistent process) software that runs on the manager node, while worker daemons run on worker nodes. The manager daemon is responsible for accepting job requests from client processes, which typically run on client workstations, queuing them, partitioning them into sub-jobs or tasks, scheduling the tasks, and assigning them to the worker daemons. The worker daemons request sub-jobs from the manager daemon, execute those sub-jobs, and return results to the manager daemon.

A detailed description of each of these elements and the operation of the algorithm is provided below. All references cited herein are incorporated by reference in their entirety.

DETAILED DESCRIPTION OF INVENTION

For clarity of disclosure, and not by way of limitation, the detailed description of the invention is divided into the subsections that follow.

Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

As used herein, "a" or "an" means "at least one" or "one or more."

For the purposes of this invention, unless otherwise specified, "BLAST" refers to an algorithm based on the Basic Local Alignment Search Tool algorithm described in Altschul et al., *J. Mol. Biol.*, 215:403–410 (1990), the entirety of which is incorporated by reference herein. "NCBI BLAST" refers to version 2.1.2 of the National Center for Biotechnology Information's implementation of the BLAST algorithm, which is well-known in the art.

As used herein, "node" refers to a distinct spot or place in a computational tree or system. A node can be a CPU, a processor or a microprocessor or a functional portion thereof or a combination thereof. For example, in the context of a computing cluster, a node can be a single computer, consisting of one or more processors (CPUs) and a single shared collection of other hardware such as memory (RAM), or network card(s), etc.

As used herein, "link_hsps" refers to a subroutine in NCBI blast tool. For each query sequence and each database sequence, the routine link HSPs computed in an earlier stage between these two sequences to evaluate how similar the two sequences are. Base on the result of link_hsps, the programs decide if a gap alignment will be computed for this sequence pair.

Query Packing

In BLAST, each query search of a sequence database requires computational overhead to set up the search. Specifically, a lookup table needs to be constructed for the query. By combining several queries into one search, the amount of computational overhead per query is reduced, and the overall throughput of query processing is increased. In one embodiment, the BLAST algorithm is modified to add the capability to pack multiple query sequences into a single scanning pass of the database, thus decreasing processing time for multiple small queries while producing results that are identical with the results produced by NCBI BLAST on the same input queries. Specifically, the query lookup table is modified to contain information from several queries, along with the necessary indexing, called "query number," to link the information to its respective query.

It is important that the results of a combined query be identical to the results produced by individual searches of its constituent queries. To ensure that identical results are produced, a hash table generation is combined with scanning for multiple queries by assigning an ordinal index to each query and adding it to the hash table entries. Additionally, a separate search structure is maintained for each query for performing all post-scanning phases, including diagonal calculations such as ungapped extension, gapped extension, and alignment.

In this embodiment, a length parameter is used to determine how much query data can be combined. In prior art implementations of BLAST, a main loop received queries as input and processed one query per iteration. In this embodiment, the main loop is modified to have an inner loop that combines queries until the aggregate length of combined queries reaches or exceeds the length parameter, and performs the database search with the combined queries. The results of the combined database search comprise all of the significant word matches in all of the combined queries. The next step involves extension of these words into HSPs. The diagonal processing in this step is query specific, so all diagonal calculations are performed independently per query inside this inner loop.

In one preferred embodiment, for each query sequence Q and each database sequence D, the method of the invention performs the following processing steps.

1. Find all local alignments A1(Q,D), A2(Q,D) . . . , An(Q,D) of Q and D that exceed some threshold.
2. For the top n highest scoring database sequences D, report all alignments A1(Q,D), A2(Q,D), . . . , An(Q,D).

The BLAST specifics come at the inner step—finding the alignments. The key to the BLAST heuristic is that a statistically significant alignment is likely to contain a high scoring pair (HSP) of aligned words. The algorithm first searches for short exact matches (default length 11 for nucleotides, 3 for protein) between query sequence and database sequence. Such matches are called hits. These hits are then extended, first without gaps, then with gaps, and those HSPs that are above a given threshold are returned. The full extension step is very computationally intensive, so BLAST avoids performing unnecessary computation by only calculating full alignments for those pairs that are statistically likely to be HSPs.

One part of the algorithm that is optimized in Paracel BLAST is the way in which hit generation occurs. The algorithm for hit generation is:

1. Pre-process query, making a hash table of (n-mer, position in query where n-mer occurs).
2. Go through the database sequence and, for each n-mer, look up that n-mer in the hash table. Any positions at that index of the table are hits.

For example, suppose the query is MSLPT. Then the 3-mers are 1) MSL, 2) SLP, and 3) LPT. The hash table is shown in Table 1. Thus, a database sequence containing SLP, for example, would generate a hit at query position 2.

TABLE 1

The hash table for the query MSLPT. For each 3-mer of amino acids (AAA . . . YYY), the table contains entries for those positions in the query where that 3-mer occurs. For example, MSL occurs at position 1.

| Index | Index |
| Value | Value |
| --- | --- |
| AAA | MSL |
|  | 1 |
| AAC | . . . |
| . . . | SLP |
|  | 2 |
| LPT | . . . |
| 3 |  |
| . . . | YYY |

One of the most "expensive" (memory-consuming) data structures in the BLAST algorithm is the hash table mentioned above. At a very high level, the algorithm looks like this:

1. Populate hash table;
2. For each hit in the hash table, do more processing.

The NCBI BLAST code does not do any special management of this hash table. Paracel BLAST has re-structured the code so that whenever possible, the hash table stays in the processor's cache, rather than bouncing back and forth between processor and memory. This involves some encoding of values in the table to decrease memory usage and hence table size, so that the table fits into the cache. Since cache accesses are significantly faster than memory accesses, this results in a substantial speedup.

Dynamic Database Splitting

In the prior art, a large database to be searched could be statically split into several smaller databases. However, such a setup would require an entire BLAST search to be performed on each of the smaller databases, with no statistically valid way to combine the results of these independent searches. In one embodiment of the invention, the BLAST algorithm is modified to support splitting a search against a single large database into multiple searches against subsets of that single database without creating multiple smaller databases to represent the subsets. In this embodiment, the results are automatically recombined to produce a single BLAST report that is biologically equivalent to the report produced by searching the entire database without splitting. This modified method, referred to herein as "dynamic database splitting," requires modification to the basic BLAST algorithm in four separate areas: First, the statistical parameters need to be adjusted to generate correct partial results. Second, the input/output routines used to access the database need to be modified to support accessing a subset of the database. Third, a memory image of intermediate results needs to be produced. Fourth, these memory images need to be properly recombined to produce a single merged BLAST report.

BLAST uses the size of the database and the number of sequences in the database to calculate the statistical significance of the results produced by searching the database. To arrive at consistent results, the size in bases and number of sequences of the overall database(s) being searched must be specified. Prior art implementations of BLAST provided a command-line argument (−z) to specify the size in bases of the overall database to be used in statistical calculations, but did not provide a corresponding way to specify the number of overall sequences. In one embodiment of the invention, a new command-line option (−s) was added to specify this number, which is added to the options data structure that is referenced by the code during the search. In this embodiment, the code that calculates statistical parameters uses the value of the −s option in preference to the actual number of sequences contained in the overall database. In a further embodiment, the values for the −z and −s parameters are automatically calculated if they were not otherwise provided, based on the overall size of the subsetted database.

In one embodiment, the BLAST algorithm was modified to search a subset of a database. In a further embodiment, a subset of the database can be specified using the following nomenclature: "database#x-y", where "database" is the database name, x is the first ordinal ID ("OID") to include in the search, and y is the last OID to include in the search. In this embodiment, OID ranges from 0 to N−1, where N is the number of sequences in the database. In yet a further embodiment, a subset of the database can be specified using the following nomenclature: "database#x-y#n", where n is the number of bases in the specified subset. If n is not specified then the size of the entire database is used—this number only affects the sizing information in the report.

In this embodiment, NCBI BLAST's code was modified to reflect a basic change in the notion of a memory-mapped file in the readdb subroutine, which includes the indexfp, headerfp, and sequencefp files in the basic readdb data structure ReadDBFILE. Prior art implementations of BLAST only allowed an entire file to be mapped using the mmap(2) UNIX system call or equivalent (by calling Nlm__MemMapInit). In this embodiment, it is now possible for up to three ranges of a file to be mapped, for the header, sequence, and ambiguity sections of the index file, respectively. In this embodiment, when an index file is read in readdb_new_internal, it is initially opened without memory mapping at all. Once the number of sequences in the file is determined, the index file is closed and re-opened with two (protein) or three (DNA) ranges for memory-mapping specified. If a range of OIDs is being used, the subranges of the header and sequence files are calculated and stored in the ReadDBFILE structure by readdb_new_internal. Later they are used to map only a range of the files when they are opened in ReadDBOpenMHdrAndSeqFiles.

In one embodiment, the BLAST algorithm is modified to produce intermediate results as output instead of a final BLAST report. The intermediate results are a serialized copy of the memory image of the dynamic data structures at the point in the blastall main loop just prior to generating the alignments. In this embodiment, the dynamic data structures at this point are traversed and each memory block is stored along with embedded pointer information converted from absolute RAM addresses to relative indexes into the transcribed memory blocks. In this embodiment, no text output is produced at this stage.

In this embodiment, a program called "pbmerge" was written to read the intermediate results from multiple pieces of a large database, as described above, and to transcribe them into equivalent memory images of each by allocating dynamic memory for the memory blocks, and converting embedded memory references back from relative indices to absolute RAM addresses. The pbmerge program then combines the multiple intermediate results into a single set of results, sorts the combined results by score, and discards the lowest scoring alignments, resulting in the requested number of best matches. Finally, pbmerge executes the trailing part of the blastall main loop that was short-circuited above to produce a single merged BLAST report as output.

Linking High-Scoring Segment Pairs

As described in the Background, experimental evidence has demonstrated that the majority of computation time in BLAST is taken by extending hits, and especially in performing gapped extensions. In a typical implementation, this step occurs in a function named link_hsps( ). Even with the improvements described in the Background, a significant amount of BLAST's computational time is still spent in link_hsps( ). The function and context of link_hsps( ) is described as follows: Given a query sequence and a database, for each sequence S in the database, determine a set of HSPs H for the sequence S. The link_hsps( ) function then estimates the statistical significance of the set of HSPs H for the sequence S, and adds the sequence S to a list of most significant matches if the statistical significance exceeds a predetermined threshold. Once all of the sequences have been processed, BLAST then performs a gapped extension on the most significant matches and outputs the alignments.

In more detail, link_hsps( ) implements the following algorithm: (1) Find the highest-scoring chain C from the set of HSPs H; (2) compute the significance for C; (3) remove C from H; and (4) repeat until H is empty. The score for a chain C is calculated as follows: Given a chain C consisting of an ordered set of k HSPs $H_1, H_2, \ldots, H_k$, where $H_i$ precedes $H_{i+1}$, then:

$$score(C) = \sum_i score(H_i) - \sum_{i=1}^{k-1} connect(H_i, H_{i+1})$$

Where $score(H_i)$ is the score of that HSP and $connect(H_i, H_{i+1})$ is the penalty to connect two HSPs. Computing the maximum-scoring chain C can be performed in a computationally efficient manner based on the following observation: Let S(H) be the highest scoring chain ending at the HSP H. It follows that for the set of all H' preceding H in the chain, $$S(H) = \{h \in H'; \max(S(h) - connect(h, H))\}.$$

Figure 1:
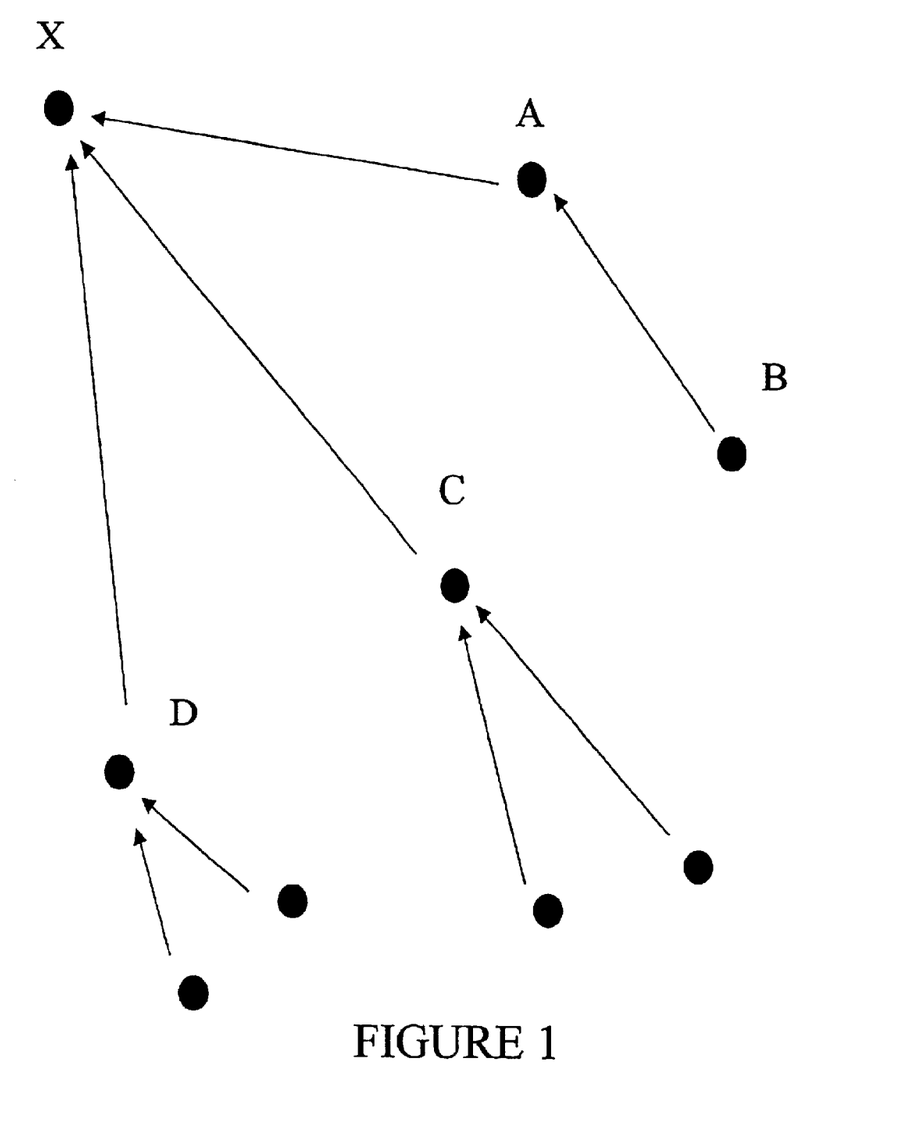
FIG. 1 provides a directed, acyclic graph representing High-scoring Segment Pairs.

In other words, the highest score of the chain ending at H is a maximum of the scores of its preceding subchains minus their respective connection penalties. It follows that if all the values S(h) are already computed, then S(H) can be readily computed. In general, for a chain of k HSPs H, there could be O(k) HSPs preceding H. This dependency is illustrated in FIG. 1. In FIG. 1, each node represents an HSP. A chain is a set of nodes connected by directed edges. If node A, is removed, node X needs to be recomputed. However, the best chain ending at C or D does not change, so S(C) and S(D) do not need to be recomputed when node A is removed.

Currently, a typical implementation of BLAST uses two connection functions, known as the large gap criterion and the small gap criterion. The large gap criterion allows large gaps to be formed, and so it sets its connection penalty to zero. The small gap criterion disallows gaps larger than a predetermined constant A. The small gap criterion sets its penalty to zero for gaps equal to or smaller than A, and to negative infinity for gaps larger than A. Current implementations require O(k) time to compute each S(h), and $O(k^2)$ time to find the highest-scoring chain ending at H. To find all chains takes up to $O(k^3)$ time. Because k grows linearly with query length, and the rest of the BLAST algorithm grows linearly with query length for a fixed database, it follows that link_hsps( ) will become the run-time bottleneck for long query sequences. As discussed elsewhere in this application, one embodiment of the invention employs "query packing," which involves the concatenation of several queries, thus increasing query length. Experimental evidence has demonstrated that for a 1 Mb query, up to 80% of computational time can be spent executing the link_hsps( ) function. In a set of HSPs H, elements with the same starting element are said to belong to the same class. As described above, one step of link_hsps( ) is to remove the highest-scoring chain C from the set of HSPs H. Because the calculation of a chain's score is performed in a manner depending on preceding points in the chain, as described above, removal of C from H requires that all C-dependent elements remaining in H be recomputed. By definition, all HSPs in a chain belong to the same class. When a chain is removed, all the remaining elements of that class need to be recomputed. In one implementation of BLAST using two separate gap criteria, each element in H belongs to two separate classes; the best chain for one criterion may contain elements from different classes in the other criterion. In current implementations, removal of the best chain of one criterion requires that all classes of the other criteria need to be recomputed. In one embodiment of the invention, the performance of link_hsps( ) is improved by avoiding this sort of recomputation.

Given a set of HSPs H, two gap criteria, and an element h in H, denote $link_1(h)$ be the previous HSP to h in the highest-scoring chain according to criterion 1 and $link_2(h)$ to be the previous HSP to h in the highest-scoring chain according to criterion 2. The forest $F_1$ is defined as the set of subtrees with $link_1(h)$ as their parent. Similarly, the forest $F_2$ is defined as the set of subtrees with $link_2(h)$ as their parent. In general, if an element h in $F_1$ is removed, only the HSPs in the subtree rooted at h need to be changed. Similarly, if a chain from $F_1$ is removed, by definition all HSPs in the chain are in one tree of $F_1$; also, because the root of that tree is also removed, the remaining HSPs in that tree need to be recomputed. However, the set of HSPs that need recomputation are not necessarily in the same tree for $F_2$. In one embodiment of the invention, instead of the entire chain being removed all at once, the individual elements of the chain to be removed are removed individually, as well as the subtree of the element removed.

After recomputation, link_hsps( ) determines the best chains in the new tree structure. A naive approach to this process would involve visiting every HSP in the trees that have changed. This approach is unnecessarily time consuming because experimental evidence has demonstrated that the number of HSPs needing recomputation tend to be a small fraction of those changed. A more efficient approach employs a heap for each tree in the forest, based on the score S(h) for each HSP. The heap allows the tree's highest-scoring chain to be determined in O(1) time. Because only the HSPs that need recomputation are visited, the total running time is $O(rm^{0.5}+r \log m)$ in the worst case, and $O(r \log m)$ in practice, where r is the number of recomputations and m is the number of HSPs. Experimental evidence indicates that r is close to $m^{1.5}$ in practice.

In one example, a 1.1 Mb query was run against a 650 Mb sequence database. The implementation of BLAST available from the National Center for Biotechnology Information ("NCBI"), version 2.1.2 required 17 hours to run. In contrast, an implementation of BLAST employing the improvements to link_hsps( ) described above finished in less than 3 hours under identical conditions.

As mentioned above, operations on the hash table—populating it and looping over it—consume a significant amount of time. This is particularly true for short queries, where only a few entries in the table will be populated. In fact, one reason that MegaBlast was developed to provide faster nucleotide vs. nucleotide searches for many small queries as described in Zhang, Z., Schwartz, S., Wagner, L. and Miller, W., A greedy algorithm for aligning DNA sequences. *Journal of Computational Biology*, 7(1–2): 203–214 (2000), the entirety of which is incorporated by reference herein. There are also several scripts available on the web, for example, that "pack" together queries, for example, putting "don't cares"—Ns for nucleotide, Xs for amino acid—between queries, running a single search, then post-processing the results to correct for offsets of the original queries within the constructed query. For example, the queries ACTG and GCGCG might be packed as ACTGNNNNNNNNNGCGCG. The point of the don't cares is to make it unlikely that a hit would occur across queries. The problem with MegaBlast and these scripts is that accuracy is lost—the statistics mean different things for a single long query and many short queries.

In accordance with one preferred embodiment, a Paracel BLAST Query Packing Algorithm maintains statistical validity with improved speed. In one embodiment, the Paracel BLAST Query Packing Algorithm works by constructing the hash of multiple queries at the same time. Instead of the hash table containing position only, it contains an ordered pair of (query number, position in query). For example, Table 1 contained the hash table created when a query Q1=MSLPT was hashed. Suppose additionally, the queries Q2=ALPTV and Q3=VMSLIC are hashed. The resulting hash table is shown in Table 2.

TABLE 2

The query-packing hash table for the queries MSLPT, ALPTV, and VMSLIC.

| Index Value | Index Value |
|---|---|
| AAA | PTV (Q2, 3) |
| AAC | ... |
| ... | SLI (Q3, 3) |
| ALP (Q2, 1) | ... |
| ... | SLP (Q1, 2) |
| LIC (Q3, 4) | ... |
| ... | VMS (Q3, 1) |
| LPT (Q1, 3)(Q2, 2) | ... |
| ... | YYY |
| MSL (Q1, 1) (Q3, 2) | |

This optimization involves modifications to the way the hash table is populated and the way hits are read out of the hash table—all subsequent processing on hits remains the same. The key is to populate the hash table with data from a packed pipeline of several queries, enough so that the hash table will be relatively full without being overcrowded. This improves performance of sets of small queries significantly. Note that unlike MegaBlast, this technique works on amino acids as well as nucleotides, so Paracel BLAST is able to run faster searches in a statistically correct way for all BLAST variants.

Implementation on Parallel Architecture

Figure 2:
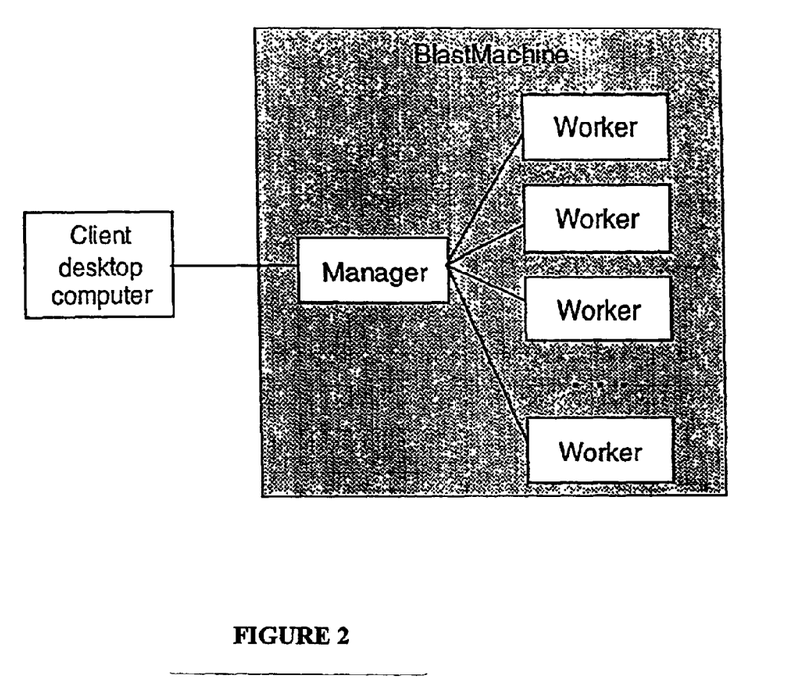
FIG. 2 illustrates a high-level block diagram of a Blast-Machine system architecture, in accordance with one embodiment of the invention.

One embodiment, an implementation of the BLAST algorithm incorporating the improvements described above is to run it on a Beowulf-class parallel processing architecture. In this embodiment, the machine performs database searches at a high rate of throughput. As queries are received, they are packed into a combined query until the size of the combined query reaches a predetermined threshold. The database to be searched is partitioned, and each processor on the machine handles the combined query search over a specific partition of the database. In a preferred embodiment, the database is dynamically partitioned so that each processor completes its search in roughly the same amount of time. The output of each database search comprises a plurality of hits, along with information linking each hit to its query in the combined query. Because the diagonal calculations for each hit are query-specific, each query's hits are then extended separately using link_hsps( ). In one embodiment, each query's hits are processed on a separate processor. In an alternate embodiment, each query's hits are extended on the same processor used to perform the database search. When all of the combined query's hits for a partition of the database have been found and extended, that partition's intermediate result is stored. Finally, the intermediate results for all database partitions are recombined and a final BLAST report is produced for each query in the combined query. In one preferred embodiment, the BlastMachine is a Beowulf-style Linux cluster, consisting of a manager node and multiple worker nodes (see FIG. 2). Each node runs Paracel BLAST, an optimized version of NCBI BLAST. The manager responds to client BLAST requests by splitting the job into smaller pieces, assigning those pieces to workers, collecting the results, and returning them to the client. Much of the complexity of the system is in the splitting and scheduling aspects, which are discussed in further detail below. BlastMachines with as few as one cpu and as many as 92 CPUs have been built. In one embodiment, each worker node is a 2-CPU Pentium III™ system.

Two performance-related problems in distributing jobs are 1) load balancing and 2) caching. To illustrate load balancing, suppose a job that takes 100 minutes on a single processor is distributed among 50 processors. If the load of each processor is the same, the job takes 2 minutes. Alternatively, suppose 49 processors receive pieces requiring 1 minute, and the final processor receives a piece requiring 51 minutes. Then the total problem takes 51 minutes, roughly half the time it required on a single CPU. Because of poor load balancing, the job may not come any where near the 50 times speedup expected based on number of processors alone. To improve this kind of pathological case, it is desirable to divide a job into as many pieces as possible. Since it is not known a priori which pieces will take the most time (a significant fraction of the time depends on the number of hits, which is not knowable without running the search), dividing into more pieces will allow faster pieces to finish sooner, and those processors may then be used for the remaining pieces. In the limit of small pieces, one might hope to break a job into such small pieces that one may achieve the actual speedup equal to the number of processors. In practice, however, there is some small amount of overhead associated with each piece, so there is a limit to how fine-grained the division can be.

A straightforward query splitting technique is to split each query into its own separate sub-jobs. Each such piece can then be scheduled independently and put on a different processor, without having to adjust statistics in subsequent steps of the BLAST algorithm. It turns out that independently scheduling each query piece—although correct—is not optimal, because it lessens the optimization provided by the query packing algorithm above. That algorithm achieves a speedup whenever multiple queries can be packed together. So the Paracel Blast manager node does some balancing—on the one hand it wants to partition as finely as possible to achieve better load balancing and utilize parallelism more efficiently; on the other hand, it wants to keep multiple queries together to optimize the speed of each piece. Depending on one's emphasis on latency or throughput, and depending on the specifics of the data involved, different strategies can be used. These strategies are discussed in further detail below.

As discussed above, in the same way Paracel Blast splits queries, it can split databases. In one embodiment, for each database D and each query Q, the Paracel BLAST algorithm finds alignments between Q and D. There is, however, a catch. To find the alignments, a statistical cutoff is used that depends on the size and number of sequences in the entire database. In one embodiment, an enhanced BLAST code allows a process manager algorithm to pass that information to each query piece. A second part of the algorithm merges all database pieces corresponding to the same query piece. For each query Q, the algorithm reports the top n database sequences in function called MERGE(D1, D2, . . . , Dm) described in further detail below. Unfortunately, this merging may sometimes produce sort orders different than those of native NCBI BLAST, as alignments with the same score are not sorted deterministically. The quality of results is the same, however, as is the statistical validity.

In one embodiment, the merge procedure is as follows: given database pieces D1, D2, . . . , Dm, and the top n alignments for each database piece, find the top n alignments overall. In a preferred embodiment, query and database splitting are mutually independent, so both optimizations can be applied simultaneously.

One benefit of database splitting is that databases can be split into pieces that are small enough to fit into RAM on the nodes. This provides two benefits:

1. The BLAST algorithm is coded in such a way that it is significantly faster if the database can stay in memory, rather than accessing it from disk or across the network, and 2. Moving databases around—particularly large ones—is expensive, so the manager tries to assign the same database piece to the same processor, thus achieving a significant speed improvement.

Database caching also allows a super linear speedup. Essentially, a job that has to load a database from disk (because it is too large to fit into memory) can be broken into n pieces, where each piece is small enough to fit into memory. The total time for a single CPU is: DB disk access+computation. For N CPUs, the total time becomes: $1/N \cdot (DB\ RAM\ access)+1/N$ computation. Since RAM access is much faster than disk access, the total time on N CPUs is less than 1/N the time for one CPU, possibly much less, and the speedup may be super-linear.

This effect is particularly striking on large jobs broken into many pieces—the first pieces run at the same speed as would be expected based on naively dividing by the number of processors. Subsequent pieces can use the cached database and are much faster. So the overall job (for longer jobs) tends toward the RAM access time, not disk access time. Note that this occurs only because the Paracel Blast manager attempts to assign different sub-jobs that use the same database piece to the same processor.

It is understood that the splitting algorithms described above apply to a set of query sequences, or combined queries, and a database comprising of multiple sequences. Individual sequences are typically not split. With available genomic sequences, however, individual sequences may be many megabases long. In one embodiment, to handle such long individual sequences, Paracel Blast uses an algorithm called Query Chopping.

Figure 3:
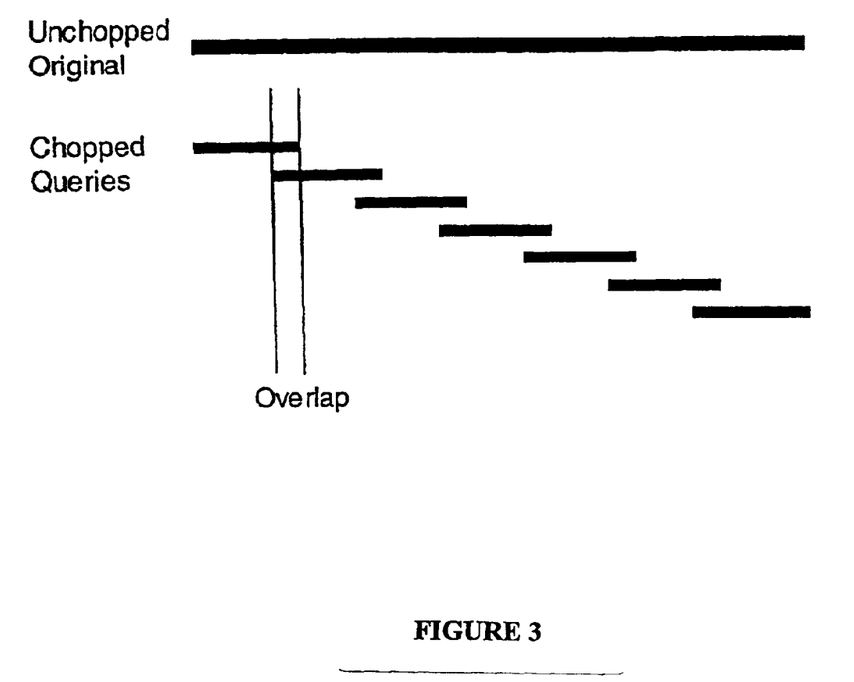
FIG. 3 illustrates a graphical representation of query chopping, in which an original query is chopped into overlapping sub-queries which can then be distributed, in accordance with one embodiment of the invention.

A naïve way to do query chopping is to manually split a long sequence into overlapping pieces and run each piece separately as shown in FIG. 3. This could even be done by a script without access to the internals of BLAST. Paracel Blast's query chopping is somewhat more sophisticated, in that it corrects for several potential problems in the overlap zone.

Figure 4:
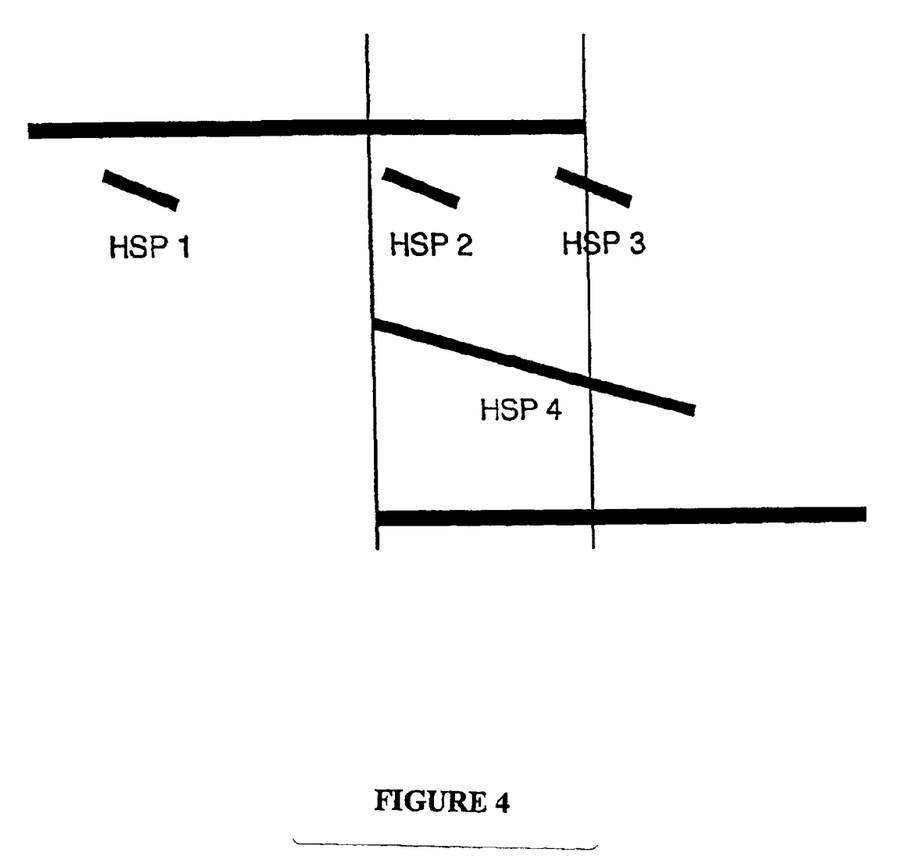
FIG. 4 illustrates a graphical representation of query chopping various HSP types, in accordance with one embodiment of the invention.

Referring to FIG. 4, after all HSPs are generated, there are three kinds: HSPs that are entirely contained in the non-overlapping regions (HSP 1), HSPs entirely contained in the overlap (HSP 2), and HSPs partially in the overlap and partially in the non-overlapping part (HSPs 3 and 4). The first class of HSPs presents no problems. The second class will be found twice—once for the left piece, once for the right. Other than the issue of only reporting them once, they present no special problem. The third class is a little trickier.

One overriding design goal is to present the same results we would obtain if there were no chopping and the entire sequence were treated as a whole. As shown in FIG. 4, any alignment that has a part in the overlap, but stops well short of the neighboring piece (e.g., HSP 3), would have stopped well short of that piece if no chopping had occurred. The only trouble is a legitimate HSP that encompasses the entire overlap, e.g., HSP 4. Such (rare) HSPs will be cut off by chopping, but can be detected as HSPs in the chopped sequences that hit both ends of the overlap (actually, come within some distance of the overlap, as there are certain edge effects).

The Paracel BLAST query chopping algorithm detects such HSPs and goes back to the original hit that led to that HSP. The original hit is extended into an HSP in the context of the unchopped query. Note that although this operation is expensive, it is exceedingly rare—it only occurs when there is an HSP that fully spans the overlap. In one preferred embodiment, Paracel BLAST uses a default overlap of 10 kilobases, so the time to recalculate these is typically very small compared to the savings gained by being able to split the query more finely and farm it out to multiple processors.

In one embodiment of the invention, Paracel BLAST includes a manager module, which partitions a job into pieces, farms each piece out to the best available worker (e.g., processor or CPU), then recombines pieces. In performing this management function the manager module considers certain competing constraints. For load balancing reasons, it would be optimal to partition into as many pieces as possible. For query chopping and database splitting, which have a merge step, excessive partitioning would require more merges and hence be inefficient. For query splitting, excessive splitting would ruin efficiencies gained by query packing. Partitioning should also take into account the number of machines—partitioning into too few pieces would leave machines idle, whereas over-partitioning—partitioning into more pieces than machines—might be desirable to improve load balancing. Additionally, there is an issue of moving data from disk over the network to the processors of the workers. For sufficiently large databases, data movement time is significant and may dominate computation time. In such cases, it may be better to partition into fewer pieces. Paracel BLAST uses a set of heuristics to do a good (but not perfect) job of handling these scheduling problems.

Experimental Results

The improvements mentioned above may be viewed independently or collectively. In the examples discussed below all BlastMachine nodes consisted of dual Pentium III™ processors running at 933 MHz with 2 GB of RAM, unless otherwise specified.

Code Optimization, Hash Table Caching, and Query Packing

To demonstrate the power of code optimization, data structure optimization, and query packing, a query data set of 50,000 25-mers (i.e., 1,250,000 bases total) taken from human chromosome 22 was run against the human reference sequences database from NCBI (10,239 sequences, 24,300,774 bases). On a 1 CPU Pentium III™ system running at 933 MHz, NCBI BLAST took 3 hours 16 minutes. On the same hardware, Paracel BLAST took 22 minutes 35 seconds—an 8.7 fold speedup.

Query Splitting

Query splitting by itself only improves latency, it does not improve throughput. However, it plays a role in all of the system benchmarks discussed below.

Database Splitting

One eighth of the human transcript database from Baylor (10,610 sequences containing 5.6 megabases) was run against the human ensemble database (30,445 sequences containing 4.4 gigabases). This search required substantial amounts of memory. In fact, NCBI BLAST 2.1.2, run on a single CPU Pentium 3 system runs out of memory and fails after 2 weeks. On a large memory, 4 CPU Alpha ES40 system, NCBI BLAST 2.1.2 runs in 214 hours and 14 minutes (almost 9 days). On a 32 CPU BlastMachine, the same search runs to completion in a mere 3 hours 17 minutes.

Query Chopping

To illustrate the power of query chopping, all the human ESTs were aligned to chromosome 22. The EST database used contains 3.7 million sequences, totaling 1.8 gigabases. Chromosome 22, obtained from the Sanger Centre, contains a single sequence of 34.6 megabases. A problem of this size cannot be run under NCBI BLAST on a typical Linux PC—it immediately runs out of memory and dies. Using Paracel BLAST's query chopping, the search ran on an 8 CPU BlastMachine in 19 minutes, 43 seconds.

C. Elegans Proteins versus NR

Several problems of interest cannot be completed in a reasonable time on conventional computers. For example, the Wormpep19 database, containing 19,105 sequences containing 8.3 million peptides from *C. elegans*, was searched against the NR database (non-redundant protein sequence database from NCBI). NR contains 582,290 sequences containing 183 million peptides. Of particular note is that one of the Wormpep sequences is a single 25,000-peptide protein. On a 1 CPU system, NCBI BLAST failed after 4 days (presumably due to memory issues related to sequence size). On a 32 CPU BlastMachine with Paracel BLAST, the same search ran to completion in 1 hour, 57 minutes.

All Human ESTs vs. All Chromosomes

One of the largest searches run to date was the alignment of all human ESTs with all human chromosomes. As above, the EST database used contains 3.7 million sequences, totaling 1.8 gigabases. The complete set of human chromosomes, obtained from UCSC, contains 3,626 sequences, totaling 3.3 gigabases. This search would not be possible without query chopping, and would be inordinately slow without all the other optimizations covered above. With Paracel BLAST on a 48 CPU BlastMachine, it ran to completion in 85 hours, 49 minutes. At present, there is not enough annotation of most of the human chromosomes to allow us to analyze the results in detail, as is being done with the ESTs and chromosome 22.

CONCLUSIONS

The Paracel BlastMachine is a system for homology search on a genomic scale. Rather than focusing on improving the sensitivity and selectivity of homology searching, it seeks to do a reasonably good job faster and for larger data sets than has been possible before. Paracel BLAST incorporates many individual optimizations that split problems and farm them out to as many nodes as possible. Each node runs code optimized to use the CPU more efficiently. The combination of query splitting, database splitting, query chopping, query packing, database caching, hash table caching, and assembly optimizations make the BlastMachine two to three orders of magnitude faster than a desktop computer (exact numbers depend on the problem and the extent to which these optimizations can be exploited).

All of the algorithmics are transparent to the user. A user submits a BLAST job through a GUI or command line, and the software automatically applies all applicable optimizations without further user intervention. The BlastMachine solves genomic-scale problems in hours, not weeks (for example, comparing a fraction of the human transcript database to the human ensemble database took just over 3 hours on a BlastMachine, compared with 9 days on an Alpha system running NCBI BLAST 2.1.2). Furthermore, Paracel BLAST partitions certain jobs automatically into manageable pieces, and hence runs searches to completion that fail on other architectures (for example placing all human ESTs on chromosomes). As ever more genomic scale data sets become available, we believe this sort of optimized tool will become increasingly useful for large-scale data analysis and mining.

The invention may be embodied in other specific forms without departing from the spirit or essential characteristics thereof. The foregoing embodiments are therefore to be considered in all respects illustrative, rather than limiting, of the invention described herein. The scope of the Invention is thus indicated by the appended claims, rather than by the foregoing description, and all variants that fall within the meaning and range of equivalency of the claims are therefore intended to be embraced therein. Furthermore, it is contemplated that the improvements described herein are not limited to sequences of biological information such as DNA and peptides, but can be applied to string searches of any kind.

What is claimed is:

1. A computer-implemented method for comparing a plurality of query sequences against a sequence database comprising the steps of:
    (a) combining said plurality of query sequences into a combined query sequence;
    (b) determining a plurality of subdivisions of said database;
    (c) performing a plurality of searches, wherein each search comprises a comparison of said combined query sequence against one of said plurality of subdivisions of said database, producing a plurality of word matches;
    (d) extending the length of plurality of word matches produced in step (c), producing a plurality of High-scoring Segment Pairs;
    (e) combining said plurality of High-scoring Segment Pairs; and
    (f) producing a plurality of reports, each report representing the highest scoring matches for one of said plurality of query sequences.

2. The method of claim 1, wherein said extending step (d) comprises the steps of:
    (i) evaluating a set of the High-scoring Segment Pairs to determine the highest-scoring chain in said set according to a first criterion, wherein said chain comprises a subset of said set of High-scoring Segment Pairs;
    (ii) removing said chain from said set of High-scoring Segment Pairs; and
    (iii) repeating said steps (i) and (ii) until said set of High-scoring Segment Pairs is empty.

3. The method of claim 2, wherein said evaluating step (i) comprises the step of determining a subset of said set of High-scoring Segment Pairs which does not requires recalculation according to a second criterion.

4. A system for conducting sequence searches in a database, which system comprises a manager node and a plurality of worker nodes, wherein said manager node is operatively linked to a client station and each of said worker nodes, and said system is capable of conducting sequence searches in a database according to the computer-implemented method of claim 1.

* * * * *